(12) United States Patent
Styrmisdottir

(10) Patent No.: US 12,027,276 B1
(45) Date of Patent: Jul. 2, 2024

(54) METHODS, SYSTEMS AND DEVICES FOR ASSESSING WOUND HEALING

(71) Applicant: DECISIONQ CORPORATION, Arlington, VA (US)

(72) Inventor: Edda Styrmisdottir, Arlington, VA (US)

(73) Assignee: DECISIONQ CORPORATION, Arlington, VA (US)

( * ) Notice: Subject to any disclaimer, the term of this patent is extended or adjusted under 35 U.S.C. 154(b) by 0 days.

(21) Appl. No.: 16/173,763

(22) Filed: Oct. 29, 2018

Related U.S. Application Data

(60) Provisional application No. 62/578,271, filed on Oct. 27, 2017.

(51) Int. Cl.
| | |
|---|---|
| G16H 50/70 | (2018.01) |
| A61B 5/00 | (2006.01) |
| G16H 10/60 | (2018.01) |
| G16H 50/20 | (2018.01) |
| G16H 50/30 | (2018.01) |
| G01N 33/68 | (2006.01) |

(52) U.S. Cl.
CPC ........... *G16H 50/70* (2018.01); *A61B 5/7275* (2013.01); *G16H 50/30* (2018.01); *G01N 33/6887* (2013.01); *G16H 10/60* (2018.01); *G16H 50/20* (2018.01)

(58) Field of Classification Search
CPC ........ G16H 10/60; G16H 50/20; G16H 50/30; G16H 50/70; A61B 5/72; A61B 5/7275; G01N 33/68; G01N 33/6887
See application file for complete search history.

(56) References Cited

U.S. PATENT DOCUMENTS

| | | | |
|---|---|---|---|
| 5,712,256 A * | 1/1998 | Kulkarni ................ | A61K 31/52 424/450 |
| 7,056,674 B2 | 6/2006 | Baker et al. | |
| 7,379,926 B1 | 5/2008 | Belniak et al. | |
| 7,526,387 B2 | 4/2009 | Baker et al. | |
| 8,510,245 B2 | 8/2013 | Stojadinovic et al. | |
| 2004/0038292 A1* | 2/2004 | Burslem ................. | A61P 11/00 435/7.1 |
| 2007/0208693 A1 | 9/2007 | Chang et al. | |
| 2008/0057590 A1 | 3/2008 | Urdea et al. | |
| 2008/0139674 A1 | 6/2008 | Archambeau et al. | |
| 2008/0144663 A1 | 6/2008 | Johnson et al. | |
| 2009/0073488 A1 | 3/2009 | Nakatomi et al. | |
| 2009/0087443 A1 | 4/2009 | Bartels | |
| 2009/0299767 A1* | 12/2009 | Michon .................. | G06Q 50/24 705/3 |
| 2010/0087756 A1 | 4/2010 | Egorov et al. | |
| 2010/0273666 A1* | 10/2010 | Bernatchez .......... | G01N 33/569 506/8 |
| 2011/0289035 A1* | 11/2011 | Stojadinovic .......... | G16B 40/00 706/45 |
| 2012/0129186 A1* | 5/2012 | Garcia ............... | G01N 33/5091 435/7.92 |
| 2013/0198119 A1* | 8/2013 | Eberhardt, III ........ | G06N 7/005 706/12 |
| 2014/0122382 A1* | 5/2014 | Elster ................... | A61B 5/7267 706/12 |
| 2016/0188833 A1* | 6/2016 | Kramer .................. | G16H 50/30 705/3 |
| 2019/0354814 A1* | 11/2019 | Schobel ................... | G06N 3/08 |

FOREIGN PATENT DOCUMENTS

| | | | | |
|---|---|---|---|---|
| EP | 3312608 A1 * | 4/2018 | ........... | C12Q 1/6883 |
| WO | WO-2004086043 A1 * | 10/2004 | ............. | A61B 5/445 |
| WO | WO-2018223001 A1 * | 12/2018 | ......... | G01N 33/6869 |

OTHER PUBLICATIONS

Guo, S., and Luisa A. DiPietro. "Factors affecting wound healing." Journal of dental research 89.3 (2010): 219-229. (Year: 2010).*
Zubair, Mohammad, Abida Malik, and Jamal Ahmad. "The impact of creatinine clearance on the outcome of diabetic foot ulcers in north Indian tertiary care hospital." Diabetes & Metabolic Syndrome: Clinical Research & Reviews 5.3 (2011): 120-125. (Year: 2011).*
Khalil, Hanan, et al. "Elements affecting wound healing time: an evidence based analysis." Wound Repair and Regeneration 23.4 (2015): 550-556. (Year: 2015).*
Reynolds, Tim M. "The future of nutrition and wound healing." Journal of tissue viability 11.1 (2001): 5-13. (Year: 2001).*
Wu, S. H., et al. "Vacuum therapy as an intermediate phase in wound closure: a clinical experience." European Journal of Plastic Surgery 23.4 (2000): 174-177. (Year: 2000).*
Hahm, George, Jacob J. Glaser, and Eric A. Elster. "Biomarkers to predict wound healing: the future of complex war wound management." Plastic and reconstructive surgery 127 (2011): 21S-26S. (Year: 2011).*
Lindley, Linsey E., et al. "Biology and biomarkers for wound healing." Plastic and reconstructive surgery 138.3 (2016): 18S. (Year: 2016).*
Stojadinovic, Alexander, et al. "Development of a Bayesian model to estimate health care outcomes in the severely wounded." Journal of multidisciplinary healthcare (2010): 125-135. (Year: 2010).*
Cancer Facts and Figures 2008, Atlanta, GA; American Cancer Society, 2009, 72 pages.
Stojadinovic A, et al., "Electrical Impedance Scanning of Thyroid Nodules Before Thyroid Surgery: A Prospective Study," Annals of Surgical Oncology, vol. 12, No. 2, 2005, pp. 152-160 (Abstract Only).

(Continued)

*Primary Examiner* — Mamon Obeid
*Assistant Examiner* — Chance L Smith
(74) *Attorney, Agent, or Firm* — ArentFox Schiff LLP

(57) ABSTRACT

The present disclosure generally relates to methods for determining the healing outcome of a wound, as well as related devices, systems and methods of treatment using a Bayesian Belief Network model that utilizes wound effluent biomarkers and clinical parameters for determining a patient-specific probability of the healing outcome of a wound.

23 Claims, 1 Drawing Sheet

(56) References Cited

OTHER PUBLICATIONS

Welker M.J., et al., "Thyroid Nodules", Am Fam Physician, vol. 67, No. 3, pp. 559-566 and 573-574, Feb. 1, 2003.
Mazzaferri, E.L., "Thyroid Cancer in Thyroid Nodules: Finding a Needle in the Haystack", The American Journal of Medicine, vol. 93, pp. 359-362, Oct. 1992.
Are C., et al., "FDG-PET Detected Thyroid Incidentalomas: Need for Further Investigation?", Annals of Surgical Oncology, vol. 14, No. 1, pp. 239-247, 2006.
Sathekge MM, et al., "Evaluation of Thyroid Nodules With Technetium-909m MIBI and Technetium-99m pertechnetate", Head & Neck, vol. 23, pp. 305-310, Apr. 2001.
Baloch, Z.W., et al., Fine-Needle Aspiration of Thyroid Nodules: Past, Present, and Future, Endocrine Practice, vol. 10, No. 3, pp. 234-241, May-Jun. 2004.
Deveci, M.S., et al., "Fine-needle aspiration of follicular lesions of the thyroid. Diagnosis and follow-Up", CytoJournal, vol. 3, No. 9, 15 pp., Apr. 7, 2006.
Varverakis E., et al., "Role of color Doppler ultrasonography in the preoperative management of cold thyroid nodules", Hormones 2007; vol. 6, No. 1, pp. 44-51, 2007.
Lyshcik, A., et al., "Quantitative Analysis of Tumor Vascularity In Benign and Malignant Solid Thyroid Nodules", J Ultrasound Med., vol. 26, No. 6, pp. 837-846, Jun. 2007.
Varverakis, E., et al., "Contribution of high-resolution ultrasonography in the differential diagnosis of benign from malignant thyroid nodules", Hormones 2002; vol. 1, pp. 51-56, 2002.
Spiezia, S., et al., "Usefulness of power Doppler in the diagnostic management of hypoechoic thyroid nodules", European Journal of Ultrasound, vol. 6, pp. 165-170, 1997.
Rago, T., et al., "Role of conventional ultrasonography and color flow-doppler sonography in predicting malignancy in 'cold' thyroid nodules", European Journal of Endocrinology, vol. 138, No. 1, pp. 41-46, Jan. 1998.
Bae, U, et al., "Ultrasound Thyroid Elastography Using Carotid Artery Pulsation, Preliminary Study", Journal of Ultrasound Medicine, vol. 26, No. 6, pp. 797-805, Jun. 2007.
Rago, T, et al., "Elastography: New Developments in Ultrasound for Predicting Malignancy in Thyroid Nodules", Journal of Clinical Endocrinology Metabolism, vol. 92, No. 8, pp. 2917-2922, Aug. 2007.
Sebastianes, F.M., et al., "Role of 18F-Fluorodeoxyglucose Positron Emission Tomography in Preoperative Assessment of Cytologically Indeterminate Thyroid Nodules", Journal of Clinical Endocrinology Metabolism, vol. 92, No. 11, pp. 4485-4488, Nov. 2007.
De Geus-Oei, et al., "18 F-FDG PET reduces unnecessary hemithyroidectomies for thyroid nodules with indeterminate cytologic results", Journal of Nucl Med., vol. 47, pp. 770-775, 2006.
Fricke, H., et al., "The Electric Resistance And Capacity of Blood for Frequencies Between 800 and 4 1/2 Million Cycles", Journal of General Physiology, pp. 153-167, 1925.
Scholz B., et al., "On Electrical Impedance Scanning—Principles and Simulations", Electromedica, vol. 68, pp. 35-44, 2000.
Glickman, Y.A., et al., "Electrical impedance scanning: a new approach to skin cancer diagnosis", Skin Research and Technology, vol. 9, pp. 262-268, 2003.
Malich A, et al., "Electrical impedance scanning: a new technique in the diagnosis of lymph nodes in which malignancy is suspected on ultrasound", Br J Radio., vol. 74, pp. 42-47. 2001.
Malich, A., et al., "Use of electrical impedance scanning in the differentiation of sonographically suspicious and highly suspicious lymph nodes of the head-neck region", Eur Radiol., vol. 12, pp. 1114-1120, 2002.
Mentzel, H.J., et al., "Electrical impedance scanning-application of this new technique for lymph node evaluation in children", Pediatr Radiol., vol. 33, pp. 461-466, 2003.
Malich A, et al., "Electrical impedance scanning for classifying suspicious breast lesions: first results", Eur Radiol., vol. 10, pp. 1555-1561, 2000.
Malich, A., et al., "Differentation of Mammographically Suspicious Lesions: Evaluation of Breast Ultrasound, MRI Mammography and Electrical Impedance Scanning as Adjunctive Technologies in Breast Cancer Detection", Clinical Radiology, vol. 56, pp. 278-283, 2001.
Fuchsjaeger, M.H., et al., "The Negative Predictive Value of Electrical Impedance Scanning in BI-RADS Category IV Breast Lesions", Invest Radiol., vol. 40, No. 7, pp. 478-485, Jul. 2005.
Stojadinovic, A., et al., "Electrical Impedance Scanning for the Early Detection of Breast Cancer in Young Women: Preliminary Results of a Multi-Center Prospective Clinical Trial", Journal of Clinical Oncology, vol. 23, No. 12, pp. 2703-2715, Apr. 20, 2005.
Stojadinovic, A., et al., "Prospective Study of Electrical Impedance Scanning for Identifying Young Women at Risk for Breast Cancer", Br Cancer Res Treat, vol. 97, No. 2, pp. 179-189, 2005.
Tuttle, R.M., et al., "Clinical Features Associated with an Increased Risk of Thyroid Malignancy in Patients with Follicular Neoplasia by Fine-Needle Aspiration", Thyroid, vol. 8, No. 5, pp. 377-383, 1998.
Montgomery, S.P., et al., "The Evaluation of Casualties from Operation Iraqi Freedom on Return to the Continental United States from Mar. to Jun. 2003", J Am Coll Surg, vol. 201, No. 1, pp. 7-12; discussion pp. 12-13, 2005.
Peoples, G.E., et al., Caring for the Wounded in Iraq—A Photo Essay, N Engl J Med, vol. 351, No. 24, pp. 2476-2480, 2004.
Owens, B.D., et al., "Combat Wounds in Operation Iraqi Freedom and Operation Enduring Freedom", J Trauma, vol. 64, pp. 295-299, 2008.
Marsh, D.J., et al., "The Role of Vacuum-Assisted Wound Closure in Blast Injury", Plast Reconstr Surg, vol. 119, pp. 1978-1979, 2007.
Breugem, C.C., et al., "Is There Evidence-Based Guidance for Timing of Soft Tissue Coverage of Grade III B Tibia Fractures?", Int J Low Extrem Wounds, vol. 5, No. 4, pp. 261-270, 2006.
Nwomeh, B.C., et al., "Physiology of the Chronic Wound", Clin Plast Surg, vol. 25, pp. 341-356, 1998.
Delong, W.G., Jr., et al., "Cytokines in Patients With Polytrauma", Clin Orthop Relat Res, No. 22, pp. 57-65, 2004.
Nast-Kolb, D., et al., "Indicators of the Posttraumatic Inflammatory Response Correlate with Organ Failure in Patients with Multiple Injuries", J Trauma, vol. 42, No. 3, pp. 446-455, Mar. 1997.
Endo, S., et al., "Plasma Endotoxin and Cytokine Concentrations in Patients with Hemorrhagic Shock", Crit Care Med, vol. 22, No. 6, pp. 949-955, 1994.
Martin, C., et al., "Patterns of cytokine evolution (tumor necrosis factor-alpha and interleukin-6) after septic shock, hemorrhagic shock, and severe trauma," Crit Care Med, vol. 25, No. 11, pp. 1813-1819, 1997.
Biffl, W.L., et al., "Interleukin-6 in the Injured Patient. Marker of Injury or Mediator of Inflammation?", Ann Surg, vol. 224, pp. 647-664, 1996.
Neidhart, R., et al., "Relationship of Interleukin-10 Plasma Levels to Severity of Injury and Clinical Outcome in Injured Patients," J Trauma, vol. 42, pp. 863-870, discussion pp. 870-861, 1997.
Lyons, A., et al., "Major Injury Induces Increased Production of Interleukin-10 by Cells of the Immune System with a Negative Impact on Resistance to Infection," Ann Surg, vol. 226, No. 4, pp. 450-458, discussion pp. 458-460, 1997.
Regan, M.C., et al., "The Role of the Wound in Posttraumatic Immune Dysfunction", Host Defense Dysfunction in Trauma, Shock and Sepsis, pp. 1043-1049, 1993.
Robson, M.C., et al., "Wound infection. A Failure of Wound Healing Caused by an Imbalance of Bacteria," Surg Clin North Am, vol. 77, No. 3, pp. 637-650, Jun. 1997.
Medzhitov, R., "Recognition of microorganisms and activation of the immune response," Nature, vol. 449, pp. 819-826, 2007.
Dinarello, C.A., "Proinflammatory Cytokines," Chest, vol. 118, pp. 503-508, 2000.
Foex, B.A., et al., "Early cytokine response to multiple injury", Injury, vol. 24, No. 6, pp. 373-376, 1993.
Jemal, A., et al., "Cancer Statistics 2009," CA Cancer J Clin, vol. 59, No. 4, pp. 225-249, Jul.-Aug. 2009.
Saving Women's Lives: Strategies for Improving Breast Cancer Detection and Diagnosis, Joy JE, Penhoet EE, and Petit DB, eds.,

(56) References Cited

OTHER PUBLICATIONS

Institute of Medicine and National Research Council of the National Academies, National Academy Press, Washington DC, pp. 155-187, 2004.
Winchester, D.P., et al., "The National Cancer Data Base Report on Breast Carcinoma Characteristics and Outcome in Relation to Age", Cancer, vol. 78, pp. 1838-1843, 1996.
Chung, M., et al., "Younger Women with Breast Carcinoma Have a Poorer Prognosis than Older Women," Cancer, vol. 77, No. 1, pp. 97-103, 1996.
Xiong, Q., et al., "Female Patients with Breast Carcinoma Age 30 Years and Younger Have a Poor Prognosis: The M.D. Anderson Cancer Center Experience," Cancer, vol. 92, No. 10, pp. 2523-2528, 2001.
Kollias, J., et al., "Screening Women Aged Less Than 50 Years With a Family History of Breast Cancer," Eur J Cancer, vol. 34, pp. 878-883, 1998.
Tilanus-Lindhorst, M.M.A., et al., "Earlier detection of breast cancer by surveillance of women at familial risk", Eur J Cancer, vol. 36, pp. 514-519, 2000.
Carney, P.A., et al., "Individual and Combined Effects of Age, Breast Density, and Hormone Replacement Therapy Use on the Accuracy of Screening Mammography," Ann. Intern. Med, vol. 138, No. 3, pp. 168-175, 2003.
Kroenke, C.H., et al., "Functional Impact of Breast Cancer by Age at Diagnosis", J Clin Oncol, vol. 22, No. 10, pp. 1849-1856, 2004.
Warner, E., et al., "Surveillance of BRCA1 and BRCA2 Mutation Carriers With Magnetic Resonance Imaging, Ultrasound, Mammography, and Clinical Breast Exam", JAMA, vol. 292, No. 11, pp. 1317-1325, 2004.
Morris, E.A., et al., "MR Imaging of the Breast in Patients with Occult Primary Breast Carcinoma", Radiology, vol. 205, pp. 437-440, 1997.
Orel, S.G., et al., "Suspicious Breast Lesions: MR Imaging with Radiologic-Pathologic Correlation", Radiology, vol. 190, pp. 485-493, 1994.
Visvanathan, K., et al., "American Society of Clinical Oncology Clinical Practice Guideline Update on the Use of Pharmacologic Interventions Including Tamoxifen, Raloxifene, and Aromatase Inhibition for Breast Cancer Risk Reduction", J Clin Oncol., vol. 27, No. 19, pp. 3235-3258, Jul. 1, 2009.
Fisher, B., et al., "Tamoxifen for the Prevention of Breast Cancer: Current Status of the National Surgical Adjuvant Breast and Bowel Project P-1 Study", JNCI, vol. 97, No. 22, pp. 1652-1662, Nov. 16, 2005.
Grann, V.R., et al., "Decision Analysis of Tamoxifen for the Prevention of Invasive Breast Cancer," Cancer J Sci Am, vol. 6, pp. 169-178, 2000.
Hershman, D., et al., "Outcomes of Tamoxifen Chemoprevention for Breast Cancer in Very High-Risk Women: A Cost-Effectiveness Analysis," J Clin Oncol, vol. 20, No. 1 pp. 9-16, Jan. 1, 2002.
Mackarem, G., "The Effectiveness of the Gail Model in Estimating Risk for Development of Breast Cancer in Women Under 40 Years of Age," Breast Journal, vol. 7, No. 1, pp. 34-39, 2001.
Livak, K. J., et al., "Analysis of Relative gene Expression Data Using Real-Time Quantitative PCR and the 2(-Delta Delta C(T)) Method", Methods, vol. 25, pp. 402-408, 2001.
Dente, C.J., et al., "Driving Biology: The Effect Of Standardized Wound Management On Wound Biomarker Profiles", Paper Presented at the 32nd Annual Meeting of the Eastern Association of the Surgery of Trauma, Jan. 15-19, 2019, pp. 1-23.
Murphy, K., "A Brief Introduction to Graphical Models and Bayesian Networks" (1998) [retrieved on Oct. 12, 2018]. Retrieved from the internet <URL: https://www.cs.ubc.ca/-nnurphyk/Bayes/bnintro.htnnl>.
Ferghali, C.A., et al., "Cytokines In Acute And Chronic Inflammation", Front Biosci., vol. 2, Jan. 1, 1997, pp. 12-26.
Hardman, M.J., et al., "Estrogen, not intrinsic aging, is the major regulator of delayed human wound healing in the elderly", Genome Biology, vol. 9, 2008, pp. R80-R80.17.
Baloch, Z.W., et al., The National Cancer Institute Thyroid fine needle aspiration state of the science conference: a summation, CytoJournal, vol. 6, No. 6, 2008, pp. 1-17.
Raza, S.N., et al., "Risk factors for well-differentiated thyroid carcinoma in patients with thyroid nodular disease", Otolaryngology-Head and Neck Surgery, vol. 139, pp. 21-26, 2008.
Nissan, A., et al., "Prospective Trial Evaluating Electrical Impedance Scanning of Thyroid Nodules Before Thyroidectomy—Final Results", Annals of Surgery, vol. 247, No. 5, pp. 843-853, May 2008.
Jemal, A., et al., "Cancer Facts & Figures 2008", Amercian Cancer Society. 2008, pp. 1-72.

\* cited by examiner

METHODS, SYSTEMS AND DEVICES FOR ASSESSING WOUND HEALING

CROSS-REFERENCE TO RELATED APPLICATION

This application claims the benefit of U.S. Provisional Patent Application No. 62/578,271, filed on Oct. 27, 2017, the contents of which is herein incorporated by reference in its entirety.

TECHNICAL FIELD

The present disclosure generally relates to methods for determining the healing outcome of a wound, as well as related devices, systems and methods of treatment using a Bayesian Belief Network model that utilizes wound effluent biomarkers and clinical parameters for determining a patient-specific probability of the healing outcome of a wound.

BACKGROUND

Modern war injuries are characterized by devastating extremity injuries, violating soft tissue, bone, and neurovascular structures. Despite technological advances in complex wound management, appropriate timing of traumatic extremity wound closure remains subjective. Devastating trauma often violates soft tissue, bone, and neurovascular structures. Traumatic wounds are often heavily contaminated with debris and bacteria. In addition, many of these patients sustain multiple injuries and are critically ill.

For all trauma centers, complex injuries require aggressive surgical care. Serial debridement procedures are performed to remove devitalized tissue and decrease bacterial load until such wounds are definitively managed with delayed primary closure, flap coverage, or split thickness skin grafts. High-volume irrigation and negative pressure therapy with vacuum-assisted closure (V.A.C.®) application have improved wound management. Despite such improvements, wound failure rates approach 20% in patients.

Previous studies have reported some success predicting healing outcomes using Bayesian modeling of an integrated proteomic biomarker panel of wound effluent inflammation-related proteins. However, at this time the basic surgical decision regarding appropriate timing of wound closure remains subjective; this observation holds true for all healthcare settings. Poorly defined pathophysiology of acute wound failure partially contributes to the difficulties of objectively assessing wound healing. Furthermore, the decision-making process used to make wound closure determination are ill-defined. After evaluating these factors, surgeons often reach a wound status determination based on his/her experience and discretion.

BRIEF SUMMARY OF EXEMPLARY EMBODIMENTS

Current criteria for wound closure or coverage consider many subjective factors, which include the patient's general condition, injury location, adequacy of perfusion, and the gross appearance of the wound. Thus, there is considerable intra-observer variability in wound assessment and even in the hands of seasoned surgeons, some wounds ultimately fail. Unfortunately, other wounds with the biologic ability to heal will undergo unnecessary surgical debridements, adding treatment costs and exposing patients to additional anesthetic and surgical morbidity risk. In view of the foregoing, there remains a need for objective and accurate methods for determining a proper time for surgical wound closure, as well as devices and systems that can assist clinicians in the selection of a time for wound closure when treating patients. The present disclosure addresses these and other needs.

In some aspects, a computer-implemented method for determining a patient-specific wound healing outcome is provided, the method comprising generating, by a processor, a training database comprising wound effluent biomarker levels and clinical parameters from a plurality of patients having known wound healing outcomes, the biomarker levels being collected from at least one of serum, wound effluent and biopsy tissue; generating, by the processor, a Bayesian Belief Network model using data from the training database, wherein the data includes an identification of at least one conditional dependence relationship between the known wound healing outcomes and the biomarker levels and clinical parameters; receiving biomarker levels and clinical parameters that have been collected for an individual patient into the Bayesian Belief Network model; calculating, by the processor, the patient-specific wound closure time using the Bayesian Belief Network model by comparing the wound effluent biomarker levels and clinical parameters of the individual patient to reference biomarker profiles of the plurality of patients having known wound healing outcomes; and outputting a report (e.g., a text-based and/or graphical representation of the predicted patient-specific wound healing outcome from the Bayesian Belief Network model). In some exemplary aspects, the output may be saved to a file (e.g., to a database or as a text file) or provided via a graphical user interface of a computer or an electronic device for use by a clinician.

In some aspects, the wound effluent biomarker levels include cytokine expression levels for IL-2, IL-4, IL-15, IFN-γ, GM-CSF, or any combination thereof; and the clinical parameters include one or more of the following: wound size/volume; wound severity; creatinine level and/or the presence of an abnormal creatinine level; anatomical main group; nutrition route for the patient and/or a need for peripheral IV nutrition; vacuum assisted closure; current or previously administered medication(s) given to the patient; or any subset thereof.

In some aspects, the method further comprises: validating the Bayesian Belief Network model; and/or updating the Bayesian Belief Network model using the biomarker levels and clinical parameters for the individual patient and the patient-specific probability of impaired wound healing.

The Bayesian Belief Network model used by any of the methods, systems or devices described herein may comprise a directed acyclic graph including a plurality of nodes, wherein each of the nodes includes at least two bins with each bin representing a value range of a biomarker level or clinical parameter associated with that node. The Bayesian Belief Network model may also be configured to predict a probability of impaired wound healing after closure of the wound at the next washout. For example, the probability of impaired wound healing may comprise a prediction regarding whether a wound will heal or dehisce if it is closed at the next washout (e.g., within 24-48 hours). In some exemplary aspects the Bayesian Belief Network may use the biomarker levels and clinical parameters for the individual patient to predict a recommended wound closure time comprising a recommended time when the wound should be closed within the ranges of 1-24, 24-48 or 48-72 hours.

In other aspects, systems for determining a patient-specific wound healing outcome is provided, comprising at least one processor configured to execute instructions for carrying out any or all of the steps of the methods described herein. Such systems may be configured to further include a graphical user interface. The Bayesian Belief Network model may be executed by the same system which provides a graphical user interface or other form of output to a clinician or executed by a system separate from that which provides the patient-specific output to a clinician as a separate unit (e.g., as part of a communicatively linked client-server model).

In still further aspects, methods of treating a wound of a patient in need thereof are provided, comprising wherein a wound closure procedure is performed on the patient in response to the output of a Bayesian Belief Network model generated in accordance with the disclosure. In some aspects, the treatment (e.g., closure of a wound at a next washout or at a recommended time) is based on a Bayesian Belief Network model trained using one or more biomarker levels comprising cytokine expression levels for IL-2, IL-4, IL-15, IFN-γ, GM-CSF cytokines, or any combination thereof; and clinical parameters which include one or more of the following: wound size/volume; creatinine level and/or the presence of an abnormal creatinine level; anatomical main group; nutrition route for the patient and/or a need for peripheral IV nutrition; vacuum assisted closure; current or previously administered medication(s) given to the patient; or any subset thereof.

The above summary of exemplary aspects serves to provide a basic understanding of the disclosure. It is understood that the individual of elements of any of the disclosed methods, systems, devices and software products may be combined to generate still further aspects without departing from the spirit of the present disclosure and the inventive aspects described herein.

BRIEF DESCRIPTION OF THE DRAWINGS

The accompanying drawings, which are incorporated into and constitute a part of this specification, illustrate one or more example aspects of the disclosure and, together with the detailed description, serve to explain their principles and implementations.

DETAILED DESCRIPTION OF EXEMPLARY EMBODIMENTS

Figure 1A:
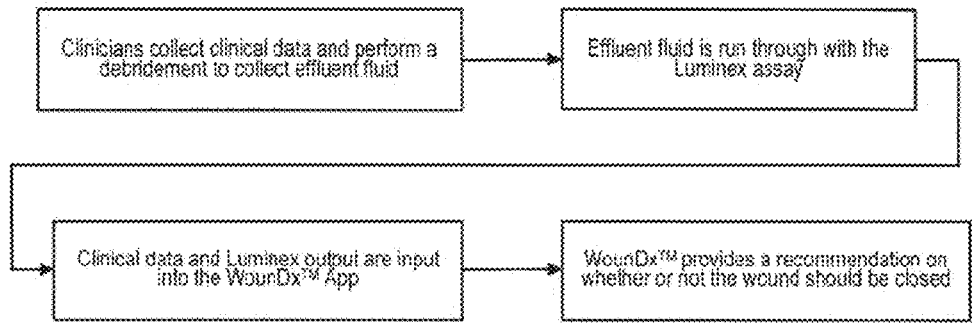
FIGS. 1A and 1B contain flow charts illustrating methods of treating a wound of a patient in need thereof using an exemplary method according to the disclosure.
Figure 1B:
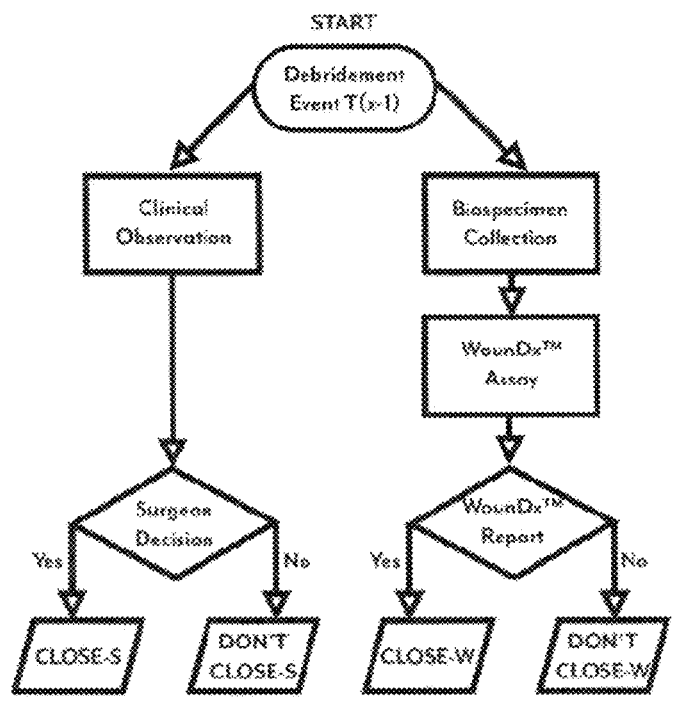

The present disclosure provides various methods, systems, devices and software products useful for accurately determining a proper time and/or likely outcomes for surgical wound closure which rely upon a Bayesian Belief Network model (referred to herein as a "BBN-ML"). As described in further detail below, a BBN-ML may be created using data from a training database comprising wound effluent biomarker levels and clinical parameters from patients, wherein the wound effluent biomarker levels may comprise one or more cytokine and/or chemokine levels (e.g., protein or RNA expression levels for one or more cytokines or chemokines) and the clinical parameters may comprise patient and/or wound characteristics, status or any other variable(s) pertinent to wound healing. In an exemplary aspect, these clinical parameters are provided to the BBN-ML in order to predict wound closure success, which may then be displayed, reported, or otherwise provided to a clinician (e.g., via a text file or a graphical user interface of a device or software). Wound effluent biomarker levels may be reflected as a presence, concentration or amount (including relative or absolute amounts) determined and/or measured at the transcriptional, translational, or post-translational stage of expression (in the case of protein biomarkers). For example, a biomarker level for a cytokine biomarker may comprise a concentration of an interleukin (IL-2, IL-4, etc.) in a sample of wound effluent or a blood serum sample obtained from a patient.

Wound Healing

The molecular landscape of the wound ultimately determines the fate of the wound healing process. Acute wounds typically heal by an interdependent sequence of events mediated by inflammatory messengers. The wound healing process generally has three phases. They are the inflammatory phase, the proliferative phase, and the maturational phase (or remodeling phase). The inflammatory phase is characterized by hemostasis and inflammation and typically lasts one to three days. After injury to tissue occurs, damaged cell membranes immediately release thromboxane A2 and prostaglandin 2-alpha, potent vasoconstrictors. This initial response helps to limit hemorrhage. After a short period, capillary vasodilatation occurs secondary to local histamine release, and the cells responsible for inflammation are able to migrate to the wound bed. The timeline for cell migration in a normal wound healing process is predictable.

Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. They act to control bleeding and limit the extent of injury. Platelet degranulation also activates the complement cascade, specifically C5a, which is a potent chemoattractant for neutrophils.

As the inflammatory phase continues, more immune response cells migrate to the wound. Neutrophil, the second response cell, is responsible for debris scavenging, complement-mediated opsonization of bacteria, and bacteria destruction via oxidative burst mechanisms (superoxide and hydrogen peroxide formation). The neutrophils kill bacteria and decontaminate the wound from foreign debris.

The next cells present in the wound are the leukocytes and the macrophages (monocytes). Macrophage is essential for wound healing. Numerous enzymes and cytokines are secreted by the macrophage, including collagenases, which debride the wound; interleukins and tumor necrosis factor (TNF), which stimulate fibroblasts (production of collagen) and promote angiogenesis; and transforming growth factor (TGF), which stimulates keratinocytes. This marks the transition into the process of tissue reconstruction, the proliferative phase.

Epithelialization, angiogenesis, granulation tissue formation, and collagen deposition are the principal steps in the proliferative phase of wound healing. Epithelialization occurs early in wound repair. If the basement membrane remains intact, the epithelial cells migrate upwards in the normal pattern, as in first-degree skin burn. The epithelial progenitor cells remain intact below the wound, and the normal layers of epidermis are restored in 2-3 days. If the basement membrane has been destroyed, similar to a second- or third-degree burn, then the wound is re-epithelialized from the normal cells in the periphery and from the skin appendages, if intact (e.g., hair follicles, sweat glands).

Angiogenesis, stimulated by TNF-alpha, is marked by endothelial cell migration and capillary formation. The new capillaries deliver nutrients to the wound and help maintain the granulation tissue bed. The migration of capillaries into the wound bed is critical for proper wound healing. The granulation phase and tissue deposition require nutrients supplied by the capillaries, and failure for this to occur results in a chronically unhealed wound. Mechanisms for modifying angiogenesis are under study and have significant potential to improve the healing process.

The final part of the proliferative phase is granulation tissue formation. Fibroblasts differentiate and produce ground substance and then collagen. The ground substance is deposited into the wound bed. Collagen is then deposited as the wound undergoes the final phase of repair. Many different cytokines are involved in the proliferative phase of wound repair. The steps and the exact mechanism of control have not been elucidated. Some of the cytokines include PDGF, insulin like growth factor (IGF), and EGF. All are necessary for collagen formation.

The final phase of wound healing is the maturational phase. The wound undergoes contraction, ultimately resulting in a smaller amount of apparent scar tissue. The entire wound healing process is a dynamic continuum with an overlap of each phase and continued remodeling. Wound reaches maximal strength at one year and result in a tensile strength that is 30% of normal skin. Collagen deposition continues for a prolonged period, but the net increase in collagen deposition plateaus after 21 days.

Proper wound healing involves a complex interaction of cells and cytokines working in concert. Particularly, cytokines and chemokines orchestrate the progression of healing and are fundamental to the cellular and biochemical events that occur during acute wound healing. These effectors can be measured in serum and wound effluent using modern molecular techniques.

Bayesian Network Models

As described more fully below, a machine-learned BBN-ML is created, updated, and deployed without human-developed decision support rules. A machine learning algorithm allows the BBN-ML to learn dynamically from data that resides in a data warehouse. The machine learning algorithm automatically detects and promotes significant relationships between variables without the need for human interaction. This allows for the processing of vast amounts of complex data quickly and easily into a tractable Bayesian network. The structure of the network provides the user with immediate knowledge about the nature of the problem set and the relative significance of variables to the outcome of interest. By inputting current knowledge into the BBN-ML, the user obtains a probability of outcome and relative risk in real-time.

In some aspects, the BBN-ML is trained using wound effluent biomarker levels and clinical parameters from patients (e.g., with known wound healing outcomes) to create a training database. As described more fully below, exemplary biomarkers include gene and/or protein expression levels for cytokines and/or chemokines including IL-1a, IL-10, IL-2, IL-3, IL-4, IL-5, IL-6, IL-7, IL-8, IL-10, IL-12(p40), IL-12(p70), IL-13, IL-15, IP-10, Eotaxin, IFN-γ, GM-CSF, MCP-1, MIP-1α, RANTES, and TNFα, or any subset thereof. In some exemplary aspects, the biomarker levels used to train the BBN-ML include gene and/or protein expression levels of biomarkers IL-2, IL-4, IL-15, IFN-γ, and GM-CSF, or any combination thereof.

Exemplary clinical parameters include one or more of the following: wound size or volume (e.g., $mm^3$), creatinine level or the presence of an abnormal creatinine level, various medications, need for peripheral IV nutrition, vacuum assisted closure, medication(s) previously or concurrently administered to the patient, or any subset thereof. Although in some embodiments, not all of the example clinical parameters are used in a particular BBN-ML.

Various exemplary wound effluent biomarkers and clinical parameters that may be used as part of the methods described herein are illustrated by Table 1 below. As illustrated by this table, biomarker levels and clinical parameters can be represented as yes/no, numeric or Boolean values.

TABLE 1

Exemplary biomarkers and clinical parameters that may be used as part of the methods described herein.

| Biomarker/Clinical Parameter Name | Definition | Variable Type |
|---|---|---|
| Abnormal Creatinine | Is the level of creatinine abnormal? Yes No | Yes/No 47% 53% |
| Anatomical Main Group - Various Medications | Was the patient at least once, constantly or never on a medication whose anatomical main group was classified as "various" At Least Once Constantly Never | "At Least Once"/ "Constantly"/ "Never" 32.7% 12.1% 55.2% |
| Effluent GM-CSF | The effluent GM-CSF level for the wound Min Max Mean | Numeric 1.53 66.7 13.07 |
| Effluent IFN-γ | The effluent IFN-γ level for the wound Min Max Mean | Numeric 2.13 74.5 10.72 |
| Effluent IL-2 | The effluent IL-2 level for the wound Min Max Mean | Numeric 0.07 18.7 5.00 |
| Effluent IL-4 | The effluent IL-4 level for the wound Min Max Mean | Numeric 3.74 38.1 13.23 |
| Effluent IL-15 | The effluent IL-5 level for the wound Min Max Mean | Numeric 4.33 1,080 224.99 |
| Nutrition Route - Peripheral IV | Is nutrition administered through a peripheral IV Checked Unchecked | Checked/ Unchecked 11.2% 88.8% |
| Vacuum Assisted Closure | Is a vacuum assisted closure currently the most severe treatment Checked Unchecked | Checked/ Unchecked 80.8% 19.2% |
| Wound Healing | Did the wound heal or dehisce? Outcome variable Dehisced Healed | Dehisced/ Healed 22.4% 77.6% |
| Wound Volume | The wound volume in unit $mm^3$ Min Max Mean | Numeric 4.2 9,600 1,348.4 |

As illustrated by Table 1, clinical parameters may include e.g., parameters related to "wound healing," "wound volume," and "vacuum assisted closure." As used herein, it is understood that the "wound healing" clinical parameters refers to whether a wound stayed completely closed after surgery or if it dehisced. Complete wound closure is defined according to the U.S. Food and Drug Administration's (FDA) Center for Devices and Radiological Health (CDRH)

as skin re-epithelization without drainage or dressing requirements, as confirmed by two consecutive visits 2 weeks apart. Wound dehiscence is defined as the rupturing of a wound along a surgical incision. With respect to the "wound volume" clinical parameter, it is understood that wound volume may be measured, e.g., by taking a picture of a wound with a scale ruler, and either a computerized volume calculating method or laser imaging area and volume calculating method may be used to calculate the volume. In other aspects, methods known in the art for measuring the volume of a wound may be used. The clinical parameter identified as "vacuum assisted closure" refers to a procedure involving insertion into a wound of a foam dressing with an open-cell structure, which is then sealed with adhesive film and connected to a vacuum pump. As indicated by Table 1, this parameter may be represented as a binary variable (e.g., checked/unchecked) indicating whether vacuum assisted closure is currently the most severe treatment for a given wound.

A BBN-ML is created using data from the training database; and, the BBN-ML is validated. In at least one embodiment, the structure of the BBN-ML is a directed acyclic graph that is learned natively from prior probabilities resident in the training database. Each node in the directed acyclic graph represents a biomarker level and/or clinical parameter and includes two or more bins. Each bin represents a value range for the wound effluent biomarker level and/or clinical parameter (e.g., bin 1: protein expression level less than or equal to 1.0; bin 2: protein expression level greater than 1.0). As described below, a node can be created such that each bin in the node includes an equal number of data points. For example, the value ranges of bins 1-3 can be created such that 33% of the training population is in each bin. In at least one embodiment, cross-validation is performed, wherein the data is randomized into groups of matched training and test data, a classifier is trained on each of the training sets created in the data preparation step using the same data discretization and modeling parameters. Then each corresponding test set is used to create a set of case-specific predictions. A Receiver-Operating Characteristic (ROC) curve is plotted for each test exercise to estimate model robustness and classification accuracy. Upon completion, the best model structure is documented in, for example, XML format for deployment as the BBN-ML. In at least one embodiment, the relevant learning parameter and modeling log files are stored if future audits are performed.

The method in at least one embodiment collects the biomarker levels and clinical parameters from an individual patient, which are received into the BBN-ML. The patient-specific probability of wound healing is output from the BBN-ML to a clinician (e.g., via a text file or graphical user interface) for use in pre-operative planning. As described more fully below, the Bayesian models may be in a format such that a relative gene and/or protein expression level can be received by the model on a system separate from that which outputs an evidence-based patient-specific prediction of diagnosis to a clinician, thus enabling patient-risk stratification and clinical intervention.

The method updates the BBN-ML using the wound effluent biomarker levels and clinical parameters from the individual patient and the patient-specific probability of wound healing. According to at least one embodiment, the ongoing process of model development and deployment is one of data collection, model development, model validation, model deployment (i.e., diagnosis), and iteration. This process is not static; it includes constant update, validation, and improvement. As new data is collected, models are updated and QC/QA documented.

An exemplary process flow for implementing a system for predicting a patient-specific probability of wound healing according to an embodiment of the disclosure may include any or all of the following steps. A clinician runs diagnostic test(s) on a patient; and, results are written to a patient database (also referred to herein as a "data warehouse" or "training database"). The database sends, for example, an XML message with raw patient diagnostic data to a batch inference application programming interface (API). The batch inference API communicates with a model (also referred to herein as the "BBN-ML"), which calculates a patient-specific prediction. The batch inference API may be configured to send XML messages with the patient-specific prediction to the clinician and to record the result in the patient database.

Exemplary Methods for Predicting a Recommended Wound Closure Time Using BBN-MLs

A BBN-ML may be used to predict the probability of impaired wound healing using a combination of wound effluent biomarkers and clinical parameters. For example, probabilistic predictive networks may be utilized to assess the healing outcome for an acute traumatic wound based on the expression level of related biomarkers such as cytokines, chemokines, and/or other genes, RNA transcripts, and translation products, alone or in combination with clinical parameters (e.g., abnormal creatinine levels, anatomical main group, need for peripheral IV nutrition, vacuum assisted closure, and wound volume (mm 3)).

As used herein, the term "anatomical main group" refers to the main group level of the Anatomical Therapeutic Chemical (ATC) Classification System, which is used for the classification of active ingredients of drugs according to the organ or system on which they act and their therapeutic, pharmacological and chemical properties. This classification system is controlled by the World Health Organization Collaborating Centre for Drug Statistics Methodology (WHOCC), and was first published in 1976. Currently, there are fourteen anatomical main groups (labelled, "A" to "V"). The "V" main group label refers to "Various" medications, a classification group which includes, e.g., subgroups V01 (Allergens), V03 (All Other Therapeutic Products), V04 (Diagnostic Agents), and V06 (General Nutrients), and V20 (Surgical Dressings). The BBN-ML and methods described herein may include clinical parameters relating to any medication classified within the "Various" anatomical main group or a subclass thereof. For example, such clinical parameters may account for whether a patient has been administered (or will be administered) a "Various" medication, or information regarding a dosage regimen or frequency of a "Various" medication. The BBN-ML and methods described herein may account for clinical parameters related to any number of "Various" medication.

In some aspects, this clinical parameter may indicate whether a patient was given any of the "Various" medications: "Constantly" if they are taking a medication meeting this classification at every washout leading to closure; "At Least Once" if they took any medications meeting the classification at least one washout but not constantly; or "Never" if they at no point had a washout where they were taking any of these medications. It is understood that alternative parameters related to duration or frequency may be used ("Weekly," "Daily," etc.).

Methods are provided for determining wound outcomes via quantification of a set of wound effluent biomarkers and clinical parameters, or a subset thereof. Exemplary biomarkers may include selected translation products (cytokines and/or chemokines) in a patient's wound effluent, as well as RNA transcripts of selected genes from the patient's wound-bed tissue. In some exemplary aspects, biomarker levels supplied to the BBN-ML may comprise levels of any of the biomarkers described herein in a patient's serum. A BBN-ML may be trained using the sample data, which compares a sample biomarker profile to the biomarker profiles of a patient population with known wound healing outcomes. An expected, a wound healing rate and/or a patient-specific probability of wound healing outcome may then be calculated using the BBN-ML. A clinician may use this result to select a wound closure time or to assess a likelihood of successful healing or dehiscing if a wound is closed (e.g., within 24-48 hours of the next washout).

Cytokine and chemokine expressions provide an insight into the molecular pathogenesis of acute wound failures. The balance between pro- and anti-inflammatory mediators during wound repair is a factor in achieving tissue homeostasis following injury. The inflammatory response supplies signals for cellular repair and is the first of several overlapping processes that constitute wound healing. However, an exaggerated inflammatory response is deleterious to wound healing. The pathogenesis of chronic wounds is a failure to progress through the normal stages of wound healing, wherein the wounds remain in a state of chronic inflammation. Acute wound failures are the likely result of a detrimental response to injury. Overproduction of the inflammatory cytokines is seen in posttraumatic inflammation. Multiple studies in trauma populations demonstrate correlations between inflammatory cytokines and negative outcomes. For example, increased IL-6 is an independent risk factor of morbidity and mortality in trauma patients. The anti-inflammatory cytokine IL-10 is also over-expressed in injured patients and is correlated with posttraumatic septic events.

In at least one embodiment of the disclosure, a set of cytokines and/or chemokines are selected as biomarkers for determining a wound healing outcome, in combination with additional clinical parameters. Serum/wound effluent samples may be collected from a patient at different time points during treatment. The levels of biomarkers in each patient serum and/or wound effluent sample may be quantified and input to the BBN-ML for statistical analysis, which determines the probability of wound healing and/or a recommended time for wound closure. The BBN-ML is constructed using reference wound effluent biomarker and clinical parameter profiles from a patient population with similar wounds and having known wound healing outcomes. In at least one embodiment, the selected cytokines and/or chemokines include IL-1α, IL-1β, IL-2, IL-3, IL-4, IL-5, IL-6, IL-7, IL-8, IL-10, IL-12(p40), IL-12(p70), IL-13, IL-15, IP-10, Eotaxin, IFN-γ, GM-CSF, MCP-1, MIP-1α, RANTES, and TNFα, or any subset thereof.

As illustrated by Table 2 below, a BBN-ML according to the present disclosure may be trained using various biomarkers. It is understood that in some aspects, the biomarker(s) may comprise genes or proteins which have a sequence associated with any of the NCBI Gene ID or UniProt accession numbers identified on Table 2 (e.g., any DNA, mRNA or protein sequences currently listed in these database entries, or a portion or fragment thereof). For example, a biomarker suitable for use in the present methods may comprise any polypeptide sequences associated with IL-4 currently identified by UniProt Accesion No. P05112 (e.g., either of the two isoforms of IL-4 reflected in this UniProt database entry) or identified as a protein encoded by NCBI Gen ID No. 3565. Similarly, with respect to gene expression based biomarkers, it is understood that mRNA transcripts produced by transcription of any of the genes identified by the database entries listed on Table 2 may be used in exemplary aspects of the presently disclosed methods.

TABLE 2

Exemplary biomarkers that may be used in the methods described herein.

| Biomarker | | UniProt Accession | NCBI Gene ID |
|---|---|---|---|
| IL-1α | | P01583 | 3552 |
| IL-1β | | P01584 | 3553 |
| IL-1RA | | P18510 | 3557 |
| IL-2 | | P60568 | 3558 |
| IL-2R | α subunit (CD25) | P01589 | 3559 |
| | β subunit (CD122) | P14784 | 3560 |
| | γ subunit (CD132) | P31785 | 3561 |
| IL-3 | | P08700 | 3562 |
| IL-4 | | P05112 | 3565 |
| IL-5 | | P05113 | 3567 |
| IL-6 | | P05231 | 3569 |
| IL-7 | | P13232 | 3574 |
| IL-8 | | P10145 | 3576 |
| IL-10 | | P22301 | 3586 |
| IL-12 | p40 subunit | P29460 | 3593 |
| | p35 subunit | P29459 | 3592 |
| IL-13 | | P35225 | 3596 |
| IL-15 | | P40933 | 3600 |
| IL-17 | | Q16552 | 3605 |
| TNF-α | | P01375 | 7124 |
| G-CSF | | P09919 | 1440 |
| GM-CSF | | P04141 | 1437 |
| IFN-α | IFN-α 1/13 | P01562 | 3439 and 3447 |
| | IFN-α 2 | P01563 | 3440 |
| | IFN-α 4 | P05014 | 3441 |
| | IFN-α 5 | P01569 | 3442 |
| | IFN-α 6 | P05013 | 3443 |
| | IFN-α 7 | P01567 | 3444 |
| | IFN-α 8 | P32881 | 3445 |
| | IFN-α 10 | P01566 | 3446 |
| | IFN-α 14 | P01570 | 3448 |
| | IFN-α 16 | P05015 | 3449 |
| | IFN-α 17 | P01571 | 3451 |
| | IFN-α 21 | P01568 | 3452 |
| IFN-γ | | P01579 | 3458 |
| EGF | | P01133 | 1950 |
| FGF-Basic | | P09038 | 2247 |
| HGF | | P14210 | 3082 |
| VEGF | | P15692 | 7422 |
| MCP-1 (CCL2) | | P13500 | 6347 |
| MIP-1α (CCL3) | | P10147 | 6348 |
| MIP-1β (CCL4) | | P13236 | 6351 |
| RANTES (CCL5) | | P13501 | 6352 |
| Eotaxin (CCL11) | | P51671 | 6356 |
| MIG (CXCL9) | | Q07325 | 4283 |
| IP-10 (CXCL10) | | P02778 | 3627 |

In some exemplary aspects, the BBN-ML is constructed using reference wound effluent biomarker and clinical parameter profiles from a patient population with similar wounds and having known wound healing outcomes, wherein the reference biomarker profiles comprise profiles for a panel of cytokines and/or chemokines including: IL-2, IL-4, IL-15, IFN-γ, and GM-CSF, or any subset thereof. The BBN-ML may also be constructed using clinical parameter profiles which account for wound size or volume (e.g., mm³), creatinine level or the presence of an abnormal creatinine level, various medications, need for peripheral IV nutrition, vacuum assisted closure, medication(s) previously or concurrently administered to the patient, or any subset thereof. In some aspects, the BBN-ML is constructed using all or any combination of the wound effluent biomarker profiles and clinical parameter profiles described herein. For example, the BBN-ML may be constructed using biomarker profiles for IL-2, IL-4, IL-15, IFN-γ, and GM-CSF and clinical parameter profiles for wound volume.

In some exemplary aspects, the BBN-ML may be configured to provide a clinician with a recommendation as to whether the wound should be closed at the next washout (e.g., within the next 24, 48 or 72 hours). In some exemplary aspects, the BBN-ML may be configured to provide a clinician with a recommendation as to whether the wound should be closed in the next 24, 48 or 72 hours, and/or a recommended wound closure time within a given timeframe (e.g., within the next 24-48 hours, 48 to 72 hours, 72-96 hours, or any combination of time-points within these ranges).

In some exemplary aspects, the expression profile of selected genes from a patient wound bed biopsy sample are quantified. The sample may be prepared in a number of ways, as is known in the art (e.g., by mRNA isolation from cells where the isolated mRNA is used as is, amplified, employed to prepare cDNA, etc.) as is known in the differential expression art. The sample is typically prepared from cells or tissue harvested from a patient to be diagnosed, using standard protocols, where cell types or tissues from which such nucleic acids may be generated include any tissue in which the genetic expression pattern to be determined exists.

A number of methods for detecting and/or quantifying the expression level of an RNA or protein in a sample are available in the art and can be employed in the practice of this aspect of the disclosure. For example, hybridization assays including Northern blotting techniques, hybridization to oligonucleotide probe arrays, oligonucleotide probe microarrays, in situ hybridization, nucleic acid amplification (e.g., reverse transcriptase-polymerase chain reaction, RT-PCR) and other analytical procedures can be employed.

While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled is employed. In these assays, a sample of target nucleic acids is first prepared from the initial sample of interest, where preparation may include labeling of the target nucleic acids via a variety of signal producing system, e.g., coupled fluorescence. Following target nucleic acid sample preparation, the sample is contacted with the array under hybridization conditions, whereby complexes are formed between target nucleic acids and complementary to probe sequences that are attached to the array surface. The presence of hybridized complexes is then detected, either qualitatively or quantitatively.

In at least one embodiment, expression profiles are generated using an array of "probe" nucleic acids, which includes a probe for each of the phenotype determinative genes whose expression is contacted with target nucleic acids, as described above. Contact is carried out under hybridization conditions, and unbound nucleic acid is removed. The resultant pattern of hybridized nucleic acid provides information regarding expression for each of the genes that have been probed, where the expression information is in terms of whether or not the gene is expressed and, typically, at what level, where the expression data (i.e., expression profile) may be both qualitative and quantitative. Alternatively, non-array based methods for quantitating the levels of one or more nucleic acids in a sample may be employed, including quantitative PCR, and the like. Where the expression profile is a protein expression profile, any convenient protein quantitation protocol may be employed, where the levels of one or more proteins in the assayed sample are determined. Representative methods include, but are not limited to, proteomic arrays, flow cytometry, standard immunoassays, etc. In any of these methods, a detectable moiety (e.g., fluorescent label) may be used for detection and/or quantification.

In exemplary aspects of the disclosure, serum and/or wound effluent biomarker levels may be quantified using a Luminex® 100 IS xMAP Bead Array Platform (Millipore Corp, Billerica, Mass.) or an ELISA (enzyme-linked immunosorbent assay) kit for human cytokine detection. For example, serum and wound effluent samples may be diluted 2-fold and 100-fold, respectively, and incubated with analyte-specific monoclonal antibodies covalently linked to uniquely fluorescent beads or to enzymatic markers. Subsequently, biotinylated monoclonal antibodies specific for the bead-linked- (or enzyme-linked-) antibody:analyte complexes may be introduced. This secondary complex may then be detected by streptavidin-phycoerythrin or by a color-changing enzymatic substrate. This procedure may be performed, e.g., using the commercially available Beadlyteg Human 22-Plex Multi-Cytokine Detection System (Millipore, Billerica, Mass.) or using an ELISA-compatible microplate photometer, according to manufacturer's instructions and using the sample dilutions specified above. In some aspects of the disclosure, serum and wound effluent biomarker levels may be quantified using a Luminex® 100 or 200 Instrument, a Luminex xMAP technology-based instrument, an Invitrogen® Human Cytokine Magnetic 5-Plex Panel, an ELISA (enzyme-linked immunosorbent assay) kit for human cytokine detection, or using any other protocols and/or devices suitable for quantifying serum and/or wound effluent biomarker levels. It is understood that other methods of detection and quantification may be used, such as ELISA.

In some aspects, the disclosure provides a BBN-ML for estimating wound healing outcomes using cytokine and chemokine biomarker expression levels. As described above, inflammatory wound effluent cytokine and chemokine expression at time of initial wound debridement is correlated with wound outcome. Patients with subsequent wound dehiscence express significantly higher initial effluent inflammatory cytokines and chemokines (IL-1β, IL-6, IL-8, IL-10, and MCP-1) compared to patients with normal healing. Corroboratively, wound biopsy gene expression of inflammatory cytokines and chemokines is elevated in dehisced wounds relative to healed wounds.

However, in a complex physiologic system, it is unusual that an individual biomarker is robustly predictive of any outcome. In addition, based on the initial observations, cytokine and chemokine profiles that favor wound healing dynamically change throughout the healing (marked by debridements) process. To describe these complex, non-obvious relationships over time, the BBN-ML is used to relate serum and effluent cytokine and chemokine concentrations to expected wound healing outcome at each surgical debridement.

Multivariate conditional dependence relationships may be identified using Bayesian modeling software (e.g., Faster-Analytics™). Bayesian probability theory relates the conditional probabilities of two or more random events in order to compute posterior probabilities. A probabilistic model is generated using the serum and wound effluent cytokine and chemokine protein data at each surgical debridement from healed patient population. A step-wise training process is used to prune included features of the Bayesian network to improve model robustness and elucidate the cytokines/chemokines with the most significant influences on wound outcome. A predicted wound healing outcome (and/or a wound closure time) may be accurately determined based upon the gene and/or protein expression levels of biomarkers IL-2, IL-4, IL-15, IFN-γ, and GM-CSF, or any subset thereof, alone or further in combination with profile data associated with the various clinical parameters described herein.

An exemplary BBN-ML for predicting wound healing (either impaired or normal) and/or a recommended closure time, may comprise a plurality of nodes wherein each node in the BBN-ML represents a biomarker level from serum or effluent at a given time-point (e.g., day 3). Specifically, each node may represent the serum or wound effluent concentration (quantitated as mean fluorescence intensity) of the individual cytokine or chemokine biomarker at specific time-points along the healing trajectory. Receiver-operating characteristics for the cross validation of the BBN-ML may be determined and used to validate the accuracy of the model.

As described above, systems implementing the predictive models of the embodiments described herein may provide output in a format such that clinicians can receive an estimate of the probability of wound healing outcome if the wound were closed at the next washout (e.g., within the next 24-48 hours).

In some embodiments, a K-fold cross-validation is used to test the BBN-ML. Cross-validation by number of patients may be performed to avoid modeling bias by omitting all serum data from the training set that would appear in the testing set. A ROC curve of these predictions is calculated to determine model robustness for predicting wound healing outcome. In a K-fold cross-validation, the original sample is partitioned into K subsamples. Of the K subsamples, a single subsample is retained as the validation data for testing the predictive models, and the remaining K−1 subsamples are used as training data. The cross-validation process is repeated K times (the folds), with each of the K subsamples used exactly once as the validation data. The K results from the folds are averaged (or otherwise combined) to produce a single estimation. Contrary to repeated random subsampling, all observations are used for both training and validation, and each observation is used for validation exactly once.

An exemplary BBN-ML for determining a wound closure outcome (dehisced or healed) according to an aspect of the disclosure may be structured such that the relative contribution of the predictors includes multiple bins (e.g., where the bins are associated with upper/lower levels of protein expression). For example, the predicted wound healing outcome may be dependent upon the protein expression levels of biomarkers IL-2, IL-4, IL-15, IFN-γ, and GM-CSF, or any combination thereof, evaluated alone or in combination with one or more clinical parameter profiles.

For the training of the BBN-ML model, data generated from clinical studies along with clinical parameters may be collected in a common database. This data may in turn be reviewed for accuracy and usability. The data may be analyzed using the BBN-ML to identify conditional dependence between clinical outcomes and specific surrogate biomarker profiles and clinical parameter profiles to establish a model of wound effluent biomarker(s) and clinical parameter(s) versus outcome dependency and quantitative, patient-specific risk stratification.

The BBN-ML allows surgeons to use a quantitative, reliable method for wound assessment rather than subjective methods in current practice, which can reduce surgeon-to-surgeon variability involved in determining the proper time for definitive wound closure. Using the patient's biomarker values, the BBN-ML provides the surgical team with an estimate of the likelihood of healing success if the wound were to be closed. Providing such a quantitative and objective measure of wound status greatly reduces intra-observer variability and improves personalized, and in some cases wound-specific, treatment of trauma patients. The BBN-ML has machine-learning capabilities in that the accuracy of the BBN-ML improves with each additional patient's biomarker information entered into the database. Thus, data from the clinical study is collected for model refinement.

The BBN-MLs support several scoring metrics for network optimization: Minimum Description Length (MDL), also known as the Bayesian Information Criterion (BIC), as well as Bayesian Scoring (BDe). Minimum Description Length scoring provides a measure of quality of a model. It trades off between goodness-of-fit and model complexity. Goodness-of-fit is measured as the likelihood of the data given the model. Model complexity equals the amount of information required to store the model, subject to an inflator/deflator set by the user. Bayesian Scoring is asymptotically equivalent to MDL scoring. MDL scoring ensures that the final model represents the most likely model given the data used for learning and the model variations under consideration.

The exemplary aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

Methods of Treatment

A BBN-ML according to any aspect of the disclosure may be used as part of or in preparation for a method of treatment. In one aspect, the method of treating a wound in an individual comprises closing the wound based on a prediction from any of the BBN-MLs described herein (e.g., a BBN-ML generated using biomarker levels of cytokine expression levels for IL-2, IL-4, IL-15, IFN-γ, GM-CSF, or any combination thereof; and clinical parameters that include one or more of the following: wound size/volume; creatinine level and/or the presence of an abnormal creatinine level; anatomical main group; nutrition route for the patient and/or a need for peripheral IV nutrition; vacuum assisted closure; current or previously administered medication(s) given to the patient; or any subset thereof).

In another aspect, a method of treating a patient suffering from a wound may comprise obtaining patient wound effluent biomarker and clinical parameters, predicting a wound healing outcome after wound closure at the next washout by providing the patient wound effluent biomarker and clinical parameters to the BBN-ML, and closing the wound based on this prediction. In some aspects, an exemplary method may include obtaining biomarker levels and clinical parameters for the patient, the biomarker levels being collected from at least one of serum, wound effluent and biopsy tissue; providing the wound effluent biomarker levels and clinical parameters to a Bayesian Belief Network model which has been generated using data from a training database, wherein the training database comprises wound effluent biomarker levels and clinical parameters from a plurality of patients having known wound healing outcomes, and the data includes an identification of at least one conditional dependence relationship between known wound healing outcomes and wound effluent biomarker levels and clinical parameters; receiving a patient-specific predicted wound healing outcome calculated by the Bayesian Belief Network model; and performing a wound closure procedure on the patient based on the received predicted patient-specific wound closure success.

In some aspects, the BBN-ML used to determine if to close a wound as part of a medical treatment is constructed using reference wound effluent biomarker and clinical parameter profiles from a patient population with similar wounds having known wound healing outcomes, wherein the reference biomarker profiles comprise profiles for a panel of cytokines and/or chemokines including: IL-2, IL-4, IL-15, IFN-γ, and GM-CSF, or any subset thereof. The BBN-ML may also be constructed using clinical parameter profiles which account for wound size, abnormal creatinine levels, various medications, need for peripheral IV nutrition, vacuum assisted closure, wound volume (e.g., mm 3), or any subset thereof. In some aspects, the BBN-ML is constructed using all or any combination of the wound effluent biomarker profiles and clinical parameter profiles described herein. For example, the BBN-ML may be constructed using biomarker profiles for IL-2, IL-4, IL-15, IFN-γ, and GM-CSF and clinical parameter profiles for wound volume.

In some aspects, the BBN-ML may be configured to provide a clinician with a recommendation as to whether the wound should be closed at the next washout.

EXEMPLARY HARDWARE/SOFTWARE
IMPLEMENTATIONS

The disclosed methods may be implemented in software, hardware or a combination thereof. In some aspects, the methods are performed as part of a client-server model wherein patient data is input into the BBN-ML and a clinician receives output from the BBN-ML via a console on a local computer or other electronic device which communicates with a server (local, remote or cloud-based) that executes the BBN-ML or stores data associated with the BBN-ML. For example, the BBN-ML may be executed or stored on a server which communicates with a software application client executed on a user device operated by a clinician, via a network (e.g., the Internet).

The invention claimed is:

1. A method for determining a patient-specific wound healing probability, said method including:
generating, by a processor, a training database comprising wound effluent biomarker levels and clinical parameters obtained from a plurality of patients having known wound healing outcomes;
training, by the processor, a Bayesian Belief Network model using data from the training database, wherein the data includes an identification of at least one conditional dependence relationship between the known wound healing outcomes and the wound effluent biomarker levels and clinical parameters obtained from the plurality of patients;
receiving wound effluent biomarker levels and clinical parameters that have been collected for an individual patient into the Bayesian Belief Network model;
calculating, by the processor, a wound healing probability for the individual patient using the Bayesian Belief Network model, by comparing the wound effluent biomarker levels and clinical parameters of the individual patient to one or more reference profiles based upon the wound effluent biomarker levels and clinical parameters of the plurality of patients having known wound healing outcomes;
outputting a patient-specific wound healing probability from the Bayesian Belief Network model to an interface or console of a computer or an electronic device for use by a clinician; and
performing a wound closure procedure on the individual patient based on the patient-specific wound healing probability;
wherein the wound effluent biomarker levels include cytokine expression levels for IL-2, IL-4, IL-15, IFN-γ, GM-CSF, or any combination thereof; and
the clinical parameters include parameters based on the following: (1) the size or volume of the wound; (2) the patient's creatinine level and/or the presence of an abnormal creatinine level; (3) the anatomical main group of medications previously administered to the patient, wherein the anatomical main group is a letter code corresponding to a main group level of the Anatomical Therapeutic Chemical (ATC) Classification System; (4) whether the patient requires peripheral IV nutrition; and (5) whether vacuum assisted closure is the most severe treatment for the wound.

2. The method of claim 1, wherein the wound effluent biomarker levels include cytokine expression levels for IL-2, IL-4, IL-15, IFN-γ, and GM-CSF.

3. The method of claim 1, further comprising:
validating the Bayesian Belief Network model.

4. The method of claim 1, wherein the Bayesian Belief Network model comprises a directed acyclic graph including a plurality of nodes, wherein each of the nodes includes at least two bins with each bin representing a value range of a wound effluent biomarker level or clinical parameter associated with that node.

5. The method of claim 1, further comprising:
updating the Bayesian Belief Network model using the wound effluent biomarker levels and clinical parameters for the individual patient and the patient-specific wound healing probability.

6. The method of claim 1, wherein the wound healing probability comprises a prediction of wound closure success if the wound is closed at a next washout.

7. The method according to claim 1, wherein wound effluent biomarker levels and clinical parameters that have been collected for an individual patient are received into the Bayesian Belief Network model using the graphical user interface of the computer or the electronic device.

8. The method of claim 1, wherein the wound effluent biomarker levels consist of cytokine expression levels for IL-2, IL-4, IL-15, IFN-γ, GM-CSF, or any combination thereof.

9. The method of claim 1, further comprising closing the wound based on the patient-specific wound healing probability.

10. The method of claim 1, wherein the wound is a traumatic extremity wound.

11. A system for determining a patient-specific wound healing probability, comprising:

a processor configured to:
  generate a training database comprising wound effluent biomarker levels and clinical parameters obtained from a plurality of patients having known wound healing outcomes;
  train a Bayesian Belief Network model using data from the training database, wherein the data includes an identification of at least one conditional dependence relationship between the known wound healing outcomes and the wound effluent biomarker levels and clinical parameters obtained from the plurality of patients;
  receive wound effluent biomarker levels and clinical parameters that have been collected for an individual patient into the Bayesian Belief Network model;
  calculate a wound healing probability for the individual patient using the Bayesian Belief Network model by comparing the biomarker levels and clinical parameters of the individual patient to one or more reference profiles based upon the wound effluent biomarker levels and clinical parameters of the plurality of patients having known wound healing outcomes; and
  output a patient-specific wound healing probability from the Bayesian Belief Network model to an interface or console of a computer or an electronic device for use by a clinician; and
a computer or an electronic device configured to:
  receive the output; and
  display the received output to a clinician;
wherein the wound effluent biomarker levels include cytokine expression levels for IL-2, IL-4, IL-15, IFN-γ, GM-CSF, or any combination thereof; and
the clinical parameters include parameters based on (1) the size or volume of the wound; (2) the patient's creatinine level and/or the presence of an abnormal creatinine level; (3) the anatomical main group of medications previously administered to the patient, wherein the anatomical main group is a letter code corresponding to a main group level of the Anatomical Therapeutic Chemical (ATC) Classification System; (4) whether the patient requires peripheral IV nutrition; and (5) whether vacuum assisted closure is the most severe treatment for the wound.

12. The method of claim 11, wherein the wound effluent biomarker levels include cytokine expression levels for IL-2, IL-4, IL-15, IFN-γ, and GM-CSF.

13. A method of treating a wound in a patient in need thereof, comprising:
  obtaining wound effluent biomarker levels and clinical parameters for the patient;
  training a Bayesian Belief Network model using data from a training database,
    wherein the training database comprises wound effluent biomarker levels and clinical parameters obtained from a plurality of patients having known wound healing outcomes, and the data includes an identification of at least one conditional dependence relationship between known wound healing outcomes and the wound effluent biomarker levels and clinical parameters obtained from the plurality of patients;
  providing the wound effluent biomarker levels and clinical parameters for the patient to the trained Bayesian Belief Network model;
  receiving a recommended patient-specific wound closure time success probability calculated by the Bayesian Belief Network model; and
  performing a wound closure procedure on the patient based on the received patient-specific wound closure time success probability;
  wherein the wound effluent biomarker levels include cytokine expression levels for IL-2, IL-4, IL-15, IFN-γ, GM-CSF, or any combination thereof; and
  the clinical parameters include parameters based on the following: (1) the size or volume of the wound; (2) the patient's creatinine level and/or the presence of an abnormal creatinine level; (3) the anatomical main group of medications previously administered to the patient, wherein the anatomical main group is a letter code corresponding to a main group level of the Anatomical Therapeutic Chemical (ATC) Classification System; (4) whether the patient requires peripheral IV nutrition; and (5) whether vacuum assisted closure is the most severe treatment for the wound.

14. The method of claim 13, wherein the patient-specific wound closure time success probability is received via an interface or console of an electronic device or computer.

15. The method of claim 13, wherein:
  the wound effluent biomarker levels include cytokine expression levels for IL-2, IL-4, IL-IFN-γ, and GM-CSF.

16. The method of claim 15, wherein the closing of the wound occurs: within 24-48 hours of the generation of the output of the Bayesian Belief Network model and/or at a next washout of the wound.

17. The method of claim 13, wherein the wound closure time comprises a prediction of whether a wound should be closed at a next washout.

18. A method of treating a wound of a patient in need thereof, comprising:
  closing the wound based on the output of a Bayesian Belief Network model which has been trained using one or more wound effluent biomarker levels and clinical parameters obtained from a plurality of patients having known wound healing outcomes;
  wherein the wound effluent biomarker levels include cytokine expression levels for IL-2, IL-4, IL-15, IFN-γ, GM-CSF, or any combination thereof; and
  the clinical parameters include parameters based on the following: (1) the size or volume of the wound; (2) the patient's creatinine level and/or the presence of an abnormal creatinine level; (3) the anatomical main group of medications previously administered to the patient, wherein the anatomical main group is a letter code corresponding to a main group level of the Anatomical Therapeutic Chemical (ATC) Classification System; (4) whether the patient requires peripheral IV nutrition; and (5) whether vacuum assisted closure is the most severe treatment for the wound.

19. The method of claim 18, wherein the output of the Bayesian Belief Network model comprises a recommended patient-specific wound closure time success probability calculated by the Bayesian Belief Network model.

20. The method of claim 19, wherein the wound closure time comprises a prediction of whether a wound should be closed at a next washout.

21. The method of claim 19, wherein the wound is a traumatic extremity wound.

22. The method of claim 19, wherein the Bayesian Belief Network model is a directed acyclic graph comprising one or more nodes, wherein each node represents at least one of the wound effluent biomarker levels and clinical parameters obtained from the plurality of patients having known wound healing outcomes, and wherein each node includes two or more bins, each bin representing a value range for the respective at least one of the wound effluent biomarker levels and clinical parameters.

23. The method of claim 19, wherein the Bayesian Belief Network model is a directed acyclic graph comprising at least 10 nodes, wherein each node represents at least one of the wound effluent biomarker levels and clinical parameters obtained from the plurality of patients having known wound healing outcomes.

* * * * *